United States Patent [19]

Schmidt et al.

[11] Patent Number: 4,476,053
[45] Date of Patent: Oct. 9, 1984

[54] SURFACE-ACTIVE AZO COMPOUNDS

[75] Inventors: Adolf Schmidt, Cologne; Ernst Roos, Odenthal, both of Fed. Rep. of Germany

[73] Assignee: Bayer Aktiengesellschaft, Leverkusen, Fed. Rep. of Germany

[21] Appl. No.: 373,988

[22] Filed: May 3, 1982

[30] Foreign Application Priority Data

May 9, 1981 [DE] Fed. Rep. of Germany ....... 3118373

[51] Int. Cl.³ .................... B01J 27/24; C07C 107/02; C08G 63/12; C08J 9/00
[52] U.S. Cl. .................... 260/192; 260/193; 526/219; 502/167
[58] Field of Search ................. 260/192, 193

[56] References Cited

U.S. PATENT DOCUMENTS 2,520,338 8/1950 Robertson ............... 260/192
2,586,995 2/1952 Robertson ............... 260/192
4,059,574 11/1977 Hitzler et al. ............ 260/192

Primary Examiner—Floyd D. Higel
Attorney, Agent, or Firm—Connolly and Hutz

[57] ABSTRACT

Surface-active azo compounds corresponding to the following general formula

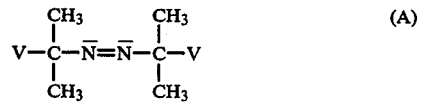

in which

V =

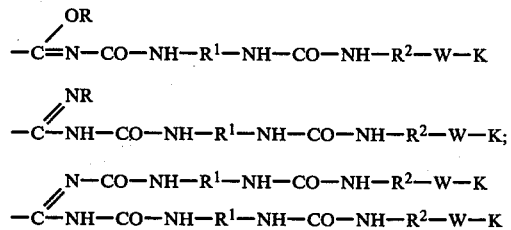

R represents $C_1-C_4$-alkyl,
$R^1$ represents the residue diminished by the isocyanate groups of an aliphatic, aromatic or cycloaliphatic diisocyanate
$R^2$ represents $C_5-C_{12}$-alkylene, phenylene
W represents $-COO^{(-)}$, $-SO_3^{(-)}$ and
K represents $Na^{(+)}$, $K^{(+)}$, $NH_4^{(+)}$, and their use in the emulsion polymerization of one or more olefinically unsaturated monomers.

2 Claims, No Drawings

SURFACE-ACTIVE AZO COMPOUNDS

This invention relates to water-soluble, surface-active substances containing azo and urea and carboxylate or sulfonate groups which may be used as emulsifying initiators for the production of low-electrolyte dispersions based on olefinically-unsaturated monomers and having a minimal tendency towards foaming.

It is known that azo diisobutyric acid amidine and derivatives thereof, for example N-alkylation or N-alkoxylation products, may be used in the form of the salts or free bases as water-soluble initiators in the emulsion polymerisation of olefinically-unsaturated monomers (cf. U.S. Pat. Nos. 2,599,300 and 2,810,702 and DE-OS No. 2,841,045).

It is also known that α,α'-azo-(α-methyl-γ-sulfo)-butyric acid dinitrile corresponding to the following formula:

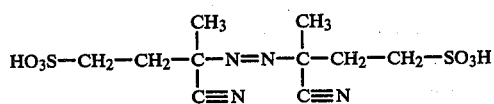

(cf. DE-AS No. 1,111,395=U.S. Pat No. 3,161,630) or α,α'-azo-(α-methyl-γ-carboxyl)-butyric acid dinitrile corresponding to the following formula:

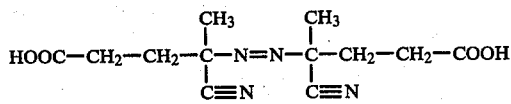

(cf. U.S. Pat. No. 2,520,338) may be used, preferably in the form of their salts, as water-soluble initiators for the polymerisation of olefinically-unsaturated monomers. However, they are not suitable for use in the emulsion polymerisation of olefinically-unsaturated monomers in the absence of standard emulsifiers for the production of stable dispersions, as demonstrated by the Comparison Tests in the present Application.

Finally, it is also known (cf. DE-OS No. 2,242,520=GB-PS No. 1,402,060) to produce azo compounds containing isocyanate groups corresponding to the following general formula:

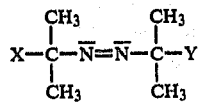

in which
X and Y are the same or different and represent the following radicals for example:

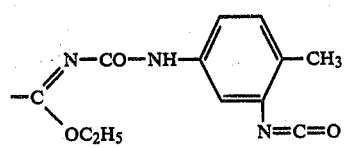

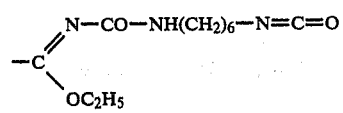

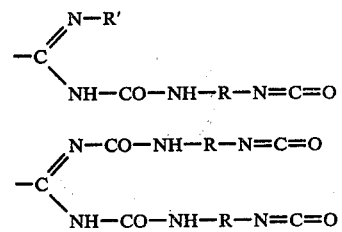

R' represents alkyl, cycloalkyl, aryl or aralkyl;
R represents alkylene, cycloalkylene, arylene, the alkylene radicals may be interrupted by a cycloaliphatic or aromatic radical whilst the polynuclear cycloalkylene or polynuclear arylene radicals may be interrupted by an aliphatic radical.

The above-mentioned compounds are used as radical formers in the production of telomers containing isocyanate groups based on olefinically-unsaturated monomers. According to the present invention, they are used as starting materials in the production of the emulsifiers containing azo groups.

The dispersions prepared in the presence of the azo initiators mentioned in the publications cited above and in the presence of emulsifiers have a tendency towards foaming. Accordingly, the object of the present invention is to provide an initiator/emulsifier system by which it is possible to prepare dispersions having a minimal tendency towards foaming. At the same time, the dispersions are required to have as low an electrolyte content as possible.

According to the invention, this object is achieved by the provision of novel surface-active azo compounds containing incorporated urea and carboxylate or sulfonate groups, which at the same time, have emulsifying and activating properties. These new substances act initially as emulsifiers and decompose during the polymerisation reaction, the catalyst fragments containing the carboxylate or sulfonate groups being incorporated into the polymer and protecting the latex particles against coagulation.

Accordingly, the present invention provides surface-active azo compounds corresponding to the following general formula (A):

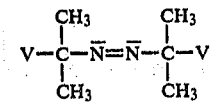

in which

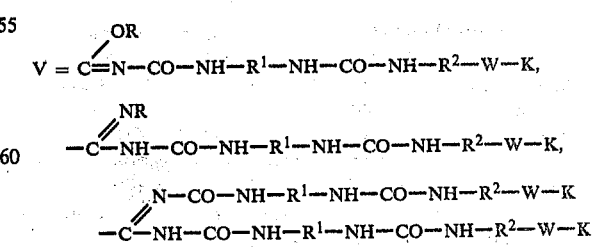

R represents $C_1$–$C_4$-alkyl,
$R^1$ represents the residue of an aliphatic, aromatic or cycloaliphatic diisocyanate without the isocyanate groups, $R^2$ represents $C_5$-$C_{12}$-alkylene or phenylene

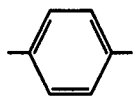

W represents —COO$^{(-)}$, —SO$_3^{(-)}$ and
K represents Na$^{(+)}$, K$^{(+)}$, NH$_4^{(+)}$.

In the above formula, V, R, $R^1$, $R^2$, W and K preferably have the following meanings:

$R = C_2H_5$
$R^1$ = the residue diminished by the isocyanate groups of 2,4- and 2,6-tolylene diisocyanate or mixtures thereof; 4,4'-diisocyanatodiphenyl methane, hexamethylene diisocyanate, 2,4,4-trimethyl-1,6-diisocyanatohexane, 1,12-dodecamethylene diisocyanate, isophorone diisocyanate
$R^2 = C_5$-$C_{12}$-alkylene, phenylene
W = —COO$^{(-)}$, —SO$_3^{(-)}$
K = Na$^{(+)}$, K$^{(+)}$.

The isocyanates (B) required for the production of the azo compounds (A) are known (cf. DE-OS No., 2,242,520 = GB-PS No. 1,402,060) or may be obtained in accordance with the publications cited above from the corresponding azoiminoethers or azoamidines and known aliphatic, cycloaliphatic or aromatic diisocyanates.

The azo compounds (A) may be produced by reacting isocyanates corresponding to the following general formula (B):

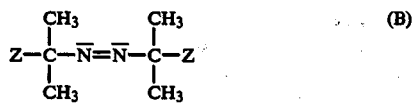

in which

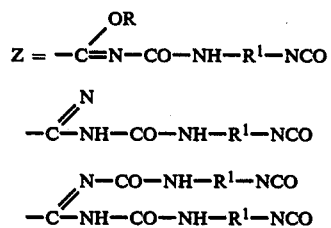

and R and $R^1$ have the same meaning as in formula (A), with substantially equivalent quantities of an alkali metal or ammonium salt of a ω-aminoalkyl carboxylic acid or ω-aminoalkylsulfonic acid containing a primary amino group and from 5 to 12 carbon atoms and preferably from 5 to 10 carbon atoms in the alkyl group or with aromatic aminosulfonic acids, such as p-aminobenzene sulfonic acid (1NH$_2$-groups $\hat{=}$ isocyanate group) in organic or organic-aqueous or aqueous solution or suspension. Where water is present, it is important to ensure that the isocyanate reacts more quickly with the primary amino groups of the amino alkyl acid than with water. The reaction may be carried out at 0° to 35° C. and preferably at 5° to 25° C.

Suitable organic solvents are tetrahydrofuran, dimethyl formamide, acetone, methylethyl ketone, dioxane, acetonitrile, dimethyl sulfoxide or mixtures thereof.

The reaction mixture may be worked up by careful evaporation to dryness. Water, methanol or ethanol is then added to the residue, the azo compounds containing carboxylate or sulfonate groups passing into solution.

Another possible method of working up the aqueous reaction mixture is to extract it with suitable water-immiscible solvents, such as low-boiling ethers.

The present invention also provides the use of the surface-active azo compounds corresponding to formula (A) in the emulsion polymerisation of one or more olefinically-unsaturated monomers for the production of low-electrolyte dispersions with a minimal tendency towards foaming. The compounds corresponding to formula (A) are used in quantities of from 1.5 to 5% by weight and preferably in quantities of from 2 to 3% by weight, based on the monomer.

The azo compounds according to the invention may be handled in the same way as standard emulsifiers during the polymerisation reaction, in other words they may be introduced all at once at the start or alternatively they may be introduced partly at the start of and partly during the emulsion polymerisation reaction (run-in process).

The polymerisation reaction is carried out at temperatures in the range of from 35° C. to 90° C., depending on the decomposition kinetics of the azo emulsifiers. The preferred temperature range is from 45° C. to 75° C.

Suitable polymerisable monomers are any olefinically-unsaturated monomers of the type which may normally be polymerised with azodiisobutyric acid nitrile, for example styrene, α-methyl styrene, butadiene, acrylic acid esters containing from 1 to 8 carbon atoms in the alcohol component, methacrylic acid esters containing from 1 to 8 carbon atoms in the alcohol component, acrylonitrile, methacrylonitrile, vinyl chloride, vinyl acetate, ethylene and chloroprene, etc.

In addition to the above-mentioned monomers, water-soluble compounds, such as methacrylic acid, acrylic acid, maleic acid semiester, itaconic acid and itaconic acid semiester, acrylamine, methacrylamide, etc., may be additionally incorporated in the polymer in relatively small quantities. In addition, it is possible to use comonomers containing functional groups, for example OH or epoxy groups, such as β-hydroxy ethyl (meth)acrylate, β-hydroxypropyl (meth)acrylate, glycidyl (meth)acrylate and N-methylol or N-methylol alkyl ethers of (meth)acrylic acid amide.

In principle, it is of course possible to use the surface-active azo compounds according to the invention in combination with standard anionic or nonionic emulsifiers.

The advantageous and surprising properties of the surface-active azo compounds according to the invention will become apparent from the following Examples and Comparison Examples.

The parts and percentages quoted in the Examples and Comparison Examples are based on weight unless otherwise indicated.

EXAMPLE 1

(Azo emulsifier 1)

A suspension of 60.4 g. (0.1 mole) of the following compound

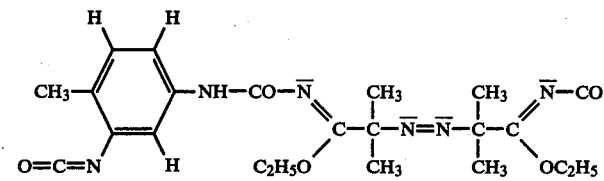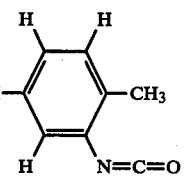

dissolved or suspended in 400 g of THF is added dropwise to a solution of 43 g (0.2 mole) of ω-aminoundecanoic acid, 11.22 g (0.2 mole) of potassium hydroxide, 200 g of water, 200 g of tetrahydrofuran (=THF), the internal temperature being kept at 25° C. After stirring for approximately 24 hours at room temperature, the reaction mixture is concentrated to dryness in vacuo to remove the tetrahydrofuran.

The dry residue is then intensively stirred for 3 hours at 30° C. with 750 ml of water to dissolve the azo emulsifier formed during the reaction. After undissolved fractions have been filtered off, the whitish filtrate is adjusted with water to a solids content of 10%. This 10% solution of the azo emulsifier is used for the emulsion polymerisation tests described in Example 2. Idealised structure of the azo emulsifier:

Weyl, Methoden der Organischen Chemie, Vol. 14/1, page 147, (1961)). The glass bottles, which had been put into fine steel baskets for protection against shattering, rotated at a speed of 25 revolutions per minute. The temperature of the water bath was kept constant. Particulars of the polymerisation reaction and the properties of the dispersions obtained are shown in Table I.

Latices having substantially the theoretical solids content (i.e. quantitative monomer conversion) are formed in every case. The coagulate content is low, as in the cases of mixtures containing highly effective anionic surfactants.

With all the latices (except for Id), the foam rapidly collapses after shaking. At 90 to 125 nm, the diameters of the latex particles are small and are of the same order of magnitude as those obtained with anionic surfactants, for example sodium laurate or sodium lauryl sulfate.

The instrument used for measuring conductivity showed the conductivity of potassium chloride solutions at room temperature as follows:

|  | C:52 | H:80 | N:10 | O:10 | K:2 | MW:1083 |
|---|---|---|---|---|---|---|
| Calculated: | 57.6 | 7.44 | 12.9 | 14.77 | 7.21 | |
| Observed: | 57.4 | 7.6 | 12.6 | 15.1 | | |

EXAMPLE 2

(Polymerisation with the emulsifier according to the invention)

Series polymerisation tests were carried out in the absence of air in 500 ml capacity corked glass bottles fitted with an additional screw cap closure (cf. Houben-

| C (mole/l) KCl | | Conductivity (ms) |
|---|---|---|
| 0.0745 g KCl/l | $10^{-3}$ | 0.12 |
| 0.746 g KCl/l | $10^{-2}$ | 1.3 |
| 7.456 g KCl/l | $10^{-1}$ | 11.2 |

TABLE I

| | Ia | Ib | Ic | Id | Ie | If | Ig | Ih |
|---|---|---|---|---|---|---|---|---|
| Deionised water, parts | 174.7 | 164.1 | 153.4 | 132.1 | 174.7 | 164.1 | 153.4 | 132.1 |
| n-Butylacrylate, parts | 0 | 0 | 0 | 0 | 57.3 | 57.3 | 57.3 | 57.3 |
| Styrene, parts | 100 | 100 | 100 | 100 | 42.7 | 42.7 | 42.7 | 42.7 |
| Azo emulsifier 1 of Example 1/ 10% in water, parts | 23.7 | 35.5 | 47.3 | 71.0 | 23.7 | 35.5 | 47.3 | 71.0 |
| Polymerisation temperature (°C.) | 60 | 60 | 60 | 60 | 60 | 60 | 60 | 60 |
| Polymerisation time (h) | 7 | 7 | 7 | 7 | 7 | 7 | 7 | 7 |
| Solids content (%) Latex | 32.6 | 33.4 | 33.5 | 34.6 | 32.1 | 32.3 | 34.2 | 34.7 |
| Coagulate (parts) | 2.4 | 1.2 | 0.8 | 0.2 | 3.1 | 3.0 | 2.6 | 1.5 |
| Electrical conductivity (mS) | 1.2 | 1.6 | 2.0 | 2.8 | 1.2 | 1.6 | 2.1 | 2.9 |
| Foam collapse (seconds) | 21 | 34 | 50 | <300 | 23 | 25 | 48 | 50 |
| Latex particle diameter (nm) | 125 | 104 | 104 | 95 | 120 | 110 | 92 | 90 |

EXAMPLE 3

(Azo emulsifier 2 according to the invention)

A suspension of 90.6 g (0.15 mole) of the following compound

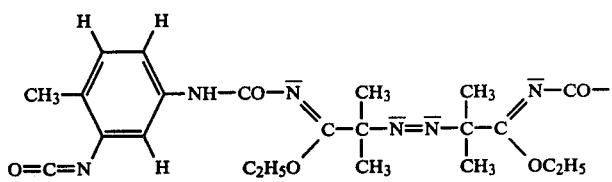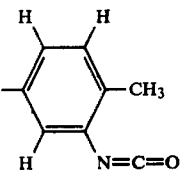

in 550 g of acetone is added dropwise over a period of about 20 minutes at +10° C. to a solution of 39.3 g of aminohexanoic acid (0.3 mole), 40 g of deionised water, 33.6 g of 50% potassium hydroxide (0.3 mole KOH) and 40 g of tetrahydrofuran. After stirring for 3 hours at room temperature, the reaction mixture is concentrated in vacuo to dryness to remove the acetone. To dissolve the azo emulsifier formed during the reaction, the dry residue is stirred for 4 hours at 25° to 30° C. with 800 ml of water, any lumps present in the reaction mixture having to be mechanically size-reduced. After undissolved fractions have been filtered off, the filtrate is adjusted with water to a solids content of 10%. This 10% solution is used for the emulsion polymerisation tests described in Example 2. Idealised structure of azo emulsifier 2

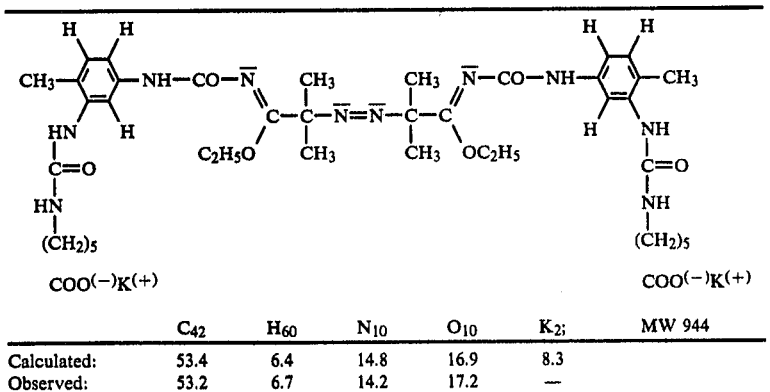

|  | C$_{42}$ | H$_{60}$ | N$_{10}$ | O$_{10}$ | K$_{2}$; | MW 944 |
|---|---|---|---|---|---|---|
| Calculated: | 53.4 | 6.4 | 14.8 | 16.9 | 8.3 | |
| Observed: | 53.2 | 6.7 | 14.2 | 17.2 | — | |

In the $^1$H NMR-spectrum measured in D$_2$O, very widespread signals for aromatic hydrogens appear at 7.0 to 7.4 ppm, the O—CH$_2$-group with its centre around 4.1 ppm, the CH$_2$-group in the α-position to acylated nitrogen around 3 ppm, the CH$_3$-group on the aromatic . . . around 2 ppm, the geminal CH$_3$-groups on the quaternary C around 1.3 ppm and the remaining CH$_2$-groups and the CH$_3$-groups from the ethoxy radical between 1.1 and 1.6 ppm.

The azo emulsifier is used for emulsion polymerisation in the same way as described in Example 2. Particulars and properties of the dispersion obtained are shown in Table II.

TABLE II

|  | IIa | IIb | IIc | IId | IIe | IIf | IIg | IIh |
|---|---|---|---|---|---|---|---|---|
| Deionised water, parts | 174.7 | 164.1 | 153.4 | 133.1 | 174.7 | 164.1 | 153.4 | 132.1 |
| n-Butylacrylate, parts | 0 | 0 | 0 | 0 | 57.3 | 57.3 | 57.3 | 57.3 |
| Styrene, parts | 100 | 100 | 100 | 100 | 42.7 | 42.7 | 42.7 | 42.7 |
| Azo emulsifier 2 of Example 3, 10% in water, parts | 23.7 | 35.5 | 47.3 | 71.0 | 23.7 | 35.5 | 47.3 | 71.0 |
| Temperature (°C.) | 60 | 60 | 60 | 60 | 60 | 60 | 60 | 60 |
| Polymerisation time (h) | 7 | 7 | 7 | 7 | 7 | 7 | 7 | 7 |
| Solids content (%) | 32.7 | 33.2 | 33.7 | 34.1 | 33.1 | 33.7 | 34.0 | 34.3 |
| Precipitate (parts) | 6.0 | 1.2 | 1.1 | 0.8 | 5.6 | 2.2 | 1.6 | 1.5 |
| Electrical conductivity (mS) | 1.1 | 1.7 | 2.1 | 2.9 | 1.2 | 1.7 | 2.1 | 3.0 |
| Foam collapse (seconds) | 60 | 59 | 40 | 37 | 13 | 17 | 23 | 46 |
| Latex particle diameter (nm) | 135 | 118 | 113 | 100 | 118 | 102 | 101 | 90 |

COMPARISON EXAMPLES (Table III)

An n-butylacrylate/styrene monomer mixture corresponding to the preceding Examples is polymerised as described in Example 2 in the presence of azodiisobutyric acid amidine; as initiator and in the presence of (a) the di-potassium salt of a standard commercial C$_{36}$-dimeric acid obtainable by polymerising unsaturated C$_{18}$-fatty acids, having the structure of a long-chain dicarboxylic acid and containing two or more alkyl side chains, acid No. 191–197, hydrolysis No. 193–200, viscosity at 25° C. 5200 mPa.s (b) the potassium salt of ω-aminohexanoic acid, (c) the potassium salt of ω-aminoundecanoic acid, as emulsifier.

The particulars and properties of the dispersions obtained are shown in Table III.

TABLE III

| | IIIa | IIIb | IIIc | IIId | IIIe | IIIf | IIIg | IIIh | IIIi | IIIk | IIIl |
|---|---|---|---|---|---|---|---|---|---|---|---|
| Deionised water, parts | 191 | 186 | 165 | 160 | 142 | 124 | 88 | 158 | 139 | 120 | 82 |
| n-Butylacrylate, parts | 57.3 | 57.3 | 57.3 | 57.3 | 57.3 | 57.3 | 57.3 | 57.3 | 57.3 | 57.3 | 57.3 |
| Styrene, parts | 42.7 | 42.7 | 42.7 | 42.7 | 42.7 | 42.7 | 42.7 | 42.7 | 42.7 | 42.7 | 42.7 |
| Azodiisobutyric acid amidine, 10% in water, parts | 5 | 5 | 5 | 8.8 | 13.1 | 17.5 | 26.2 | 6.9 | 10.4 | 13.8 | 20.8 |
| Emulsifier-dimeric acid potassium salt, 10.0% in water, parts | 5.7 | 11.3 | 34.0 | — | — | — | — | — | — | — | — |
| Potassium ω-aminohexanoate, 5% in water, parts | — | — | — | 30 | 44.8 | 59.6 | 89.4 | — | — | — | — |
| Potassium ω-aminoundecanoate 5% in water, parts | — | — | — | — | — | — | — | 33.5 | 50.2 | 66.9 | 100.3 |
| Polymerisation temperature (°C.) | 60 | 60 | 60 | 60 | 60 | 60 | 60 | 60 | 60 | 60 | 60 |
| Polymerisation time (h) | 7 | 7 | 7 | 7 | 7 | 7 | 7 | 7 | 7 | 7 | 7 |
| Solids content latex (%) | 27.2 | 31.8 | 33.9 | | | polymerisation is inhibited | | | | | |
| Coagulate in the latex (parts) | 29.3 | 20.3 | 2.2 | | | | | | | | |
| Foam collapse (seconds) | 5.6 | 7.2 | 25 | | | 2 layers instead of a latex | | | | | |
| Conductivity (mS) | 1.6 | 1.7 | 3.0 | | | | | | | | |
| Latex particle diameter (nm) | — | — | 85 | | | | | | | | |

As can be seen from Table III, latices having a high coagulate content are formed where small quantities of the dipotassium salt of dimeric acid are used as the emulsifier. At 1.6 and 1.7 mS, the electrical conductivity of these latices is comparable to that of latices If and IIf (according to the invention) of Tables I and II and their tendency tendency towards foaming is equally low. However, their coagulate content is higher by a factor of approximately 10.

If now the content of dimeric acid emulsifier is reduced to such an extent that the amount of coagulate decreases by a factor of approximately 10 (cf. Example 3c in Table III), the electrical conductivity of the dispersion is doubled and its tendency toward foaming increased. By contrast, dispersions If (Table I) and IIf (Table II) show a lower electrical conductivity for a comparable tendency towards foaming and comparable coagulate formation. If dispersions If and IIf are subsequently heat-treated, their electrical conductivity undergoes a further reduction to values of about 1.0 to 1.3 mS.

Where the potassium salts of ω-aminohexanoic acid or ω-aminoundecanoic acid are used as the emulsifier and azodiisobutyric acid amidine as the initiator (cf. Table III, Example IIId–IIIe), polymerisation of the n-butylacrylate/styrene mixture is inhibited. This is also the case when the quantity of initiator is drastically increased. Similar results are also obtained when azodiisobutyric acid iminoethyl ether is used instead of azodiisobutyric acid amide as the initiator. By contrast, low-coagulate latices with a minimal tendency towards foaming and low conductivity are obtained with the azo emulsifiers according to the invention.

COMPARISON EXAMPLES (Table IV)

The tests are carried out in the same way as in Example 2. The following "azo emulsifiers" are used:

(a) α,α'-azo-(α-methyl-γ-sulfo)-butyric acid dinitrile corresponding to the following formula:

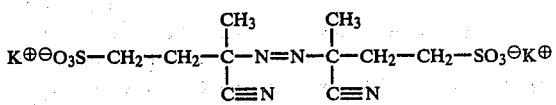

(cf. DE-AS no. 11 11 395=U.S. Pat. No. 3,161,630) and (b) α,α'-azo-(α-methyl-γ-carboxy)-butyric acid dinitrile corresponding to the following formula:

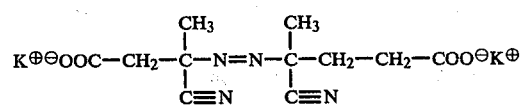

(cf. U.S. Pat. No. 2,520,338).

Particulars and results are shown in Table IV.

In no case was a latex obtained. The reaction mixtures were coagulate-containing pastes that were difficult to filter.

TABLE IV

| Deionised water | 200 | 200 | 200 | 200 | 200 | 200 |
|---|---|---|---|---|---|---|
| n-butylacrylate | 57.3 | 57.3 | 57.3 | 57.3 | 57.3 | 57.3 |
| Styrene | 42.7 | 42.7 | 42.7 | 42.7 | 42.7 | 42.7 |
| α,α'-azo-(α-methyl-γ-sulpho)butyric acid dinitrile dipotassium salt | 2.4 | 3.6 | 4.7 | — | — | — |
| α,α'-azo-(α-methyl-γ-carboxy)butyric acid dinitrile dipotassium salt | — | — | — | 2.4 | 3.6 | 4.7 |
| Polymerisation temperature (°C.) | 60 | 60 | 60 | 60 | 60 | 60 |
| Polymerisation time (h) | 7 | 7 | 7 | 7 | 7 | 7 |
| Solids content (%) | 5.2 | 10.1 | 12.8 | 6.1 | 12.5 | 18.1 |
| Coagulate | 6.1 | 4.2 | 15.0 | 10 | 7.3 | 20.0 |

EXAMPLE 4

(According to the invention)

Polybutadiene latex containing azo emulsifier 2 according to the invention:

1640 g of deionised water and 1000 g of butadiene are introduced under nitrogen into a 6 liter autoclave. The mixture is heated to 60° C., after which 360 ml of a 10% solution of azo emulsifier A (according to Example 1) are introduced under pressure into the 6 liter autoclave from a small pressure vessel.

After a polymerisation time of 6 hours, the pressure has fallen from 11.8 bars to 3.4 bars (at 60° C.). After addition of the azo emulsifier, the solids content of samples taken during polymerisation amounts to 2.0% by weight after the first hour
6.0% by weight after the second hour
15.0% by weight after the third hour
21.4% by weight after the fourth hour
30.0% by weight after the fifth hour
34.2% by weight after the sixth hour.

The latex has a latex particle diameter of approximately 90 nm. The polymer is not completely soluble in toluene. The soluble fraction has a viscosity number of 0.8 (dl/g) in toluene at 25° C. Coagulate content approximately 0.5%, based on the butadiene used. The latex has an electrical conductivity of 1.5 mS, its flow-out time from a 4 mm orifice flow-out cup according to DIN 53 211 amounting to approximately 24 seconds.

EXAMPLE 5

(According to the invention, azo emulsifier 3 and use)

10.38 g of p-aminobenzene sulfonic acid (0.06 mole) and 3.37 g of solid potassium hydroxide (0.06 mole) are dissolved in as little water as possible (approximately 30 ml). The concentrated aqueous solution is added dropwise at 25° C. to a solution of 16.9 g (0.03 mole) of the following compound

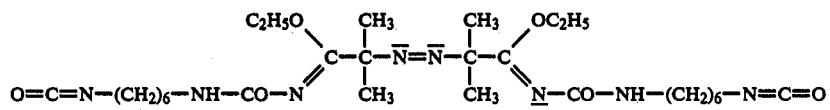

in 300 ml of tetrahydrofuran, followed by stirring for 5 hours.

After the reaction mixture has been filtered under suction, leaving approximately 4 g of water-insoluble residue, the THF-filtrate is carefully concentrated in vacuo in a rotary evaporator (approximately 30° C.).

The THF-free residue is solid and is taken up in such a quantity of water that an approximately 4.5% solution is formed. After small undissolved fractions have been filtered off, the clouded, foaming azo emulsifier filtrate is directly used as a polymerisation aid (=azo emulsifier 3).

The following constituents are introduced into a 6 liter autoclave:

1430 parts of water
573 parts of acrylic acid-n-butyl ester
427 parts of styrene
650 parts of a 4.5% solution of the above azo emulsifier 3.

The mixture is heated with stirring under nitrogen to 70° C. and kept at that temperature for 7 hours. It is then cooled to room temperature, after which the latex is run off.

The latex obtained is free from coagulate and has a solids content of approximately 33% (complete monomer conversion), an electrical conductivity of 1.5 mS, a latex particle size of 140 nm (diameter) and a minimal tendency towards foaming (foam disappears 17 seconds after vigorous shaking).

We claim:

1. A compound corresponding to the formula

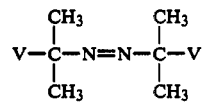

wherein
V represents the groups

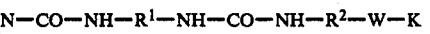

where
R represents a $C_{1-4}$ alkyl group;
$R^1$ represents that part of an aliphatic, aromatic or cycloaliphatic diisocyanate without the isocyanate groups;
$R^2$ represents a $C_{5-12}$ alkylene or a phenylene group;
W represents a $-COO^{\ominus}$ or $SO_3^{\ominus}$; and
K represents $Na^{\oplus}$, $K^{\oplus}$ or $NH_4^{\oplus}$.

2. A compound according to claim 1 wherein, in the formula
V represents

wherein
$R^1$ represents that part of 2,4- and 2,6-tolylene diisocyanate or a mixture thereof, 4,4'-diisocyanatodiphenyl methane, hexamethylene diisocyanate, 2,4,4-trimethyl-1,6-diisocyanatohexane, 1,12-dodecamethylene diisocyanate or isophorone diisocyanate without the isocyanate groups; and
K represents $Na^{\oplus}$ or $K^{\oplus}$.

* * * * *